(12) United States Patent
Sussman

(10) Patent No.: US 6,315,755 B1
(45) Date of Patent: Nov. 13, 2001

(54) METHOD OF CONTROLLING A LIQUEFRACTURE HANDPIECE

(75) Inventor: Glenn Sussman, Lake Forest, CA (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/460,919

(22) Filed: Dec. 14, 1999

Related U.S. Application Data

(63) Continuation-in-part of application No. 09/130,403, filed on Aug. 6, 1998, now abandoned, which is a continuation-in-part of application No. 09/090,433, filed on Jun. 4, 1998, now Pat. No. 6,080,128.

(51) Int. Cl.[7] .................. A61M 1/00; A61F 1/00
(52) U.S. Cl. .................. 604/28; 604/27; 606/107; 700/281; 700/282; 239/4; 239/13
(58) Field of Search .................. 700/1, 32, 39, 700/282, 281, 283, 289; 604/19–22, 27, 28, 43, 51, 54, 248; 606/107; 239/4, 13, 102.1, 132, 133, 337, 340, 428.05

(56) References Cited

U.S. PATENT DOCUMENTS

| | | |
|---|---|---|
| 3,589,363 | 6/1971 | Banko et al. .................. 128/28 |
| 3,606,878 | 9/1971 | Kellog .................. 128/276 |
| 3,818,913 | 6/1974 | Wallach .................. 128/305 |
| 3,930,505 | 1/1976 | Wallach .................. 128/305 |
| 3,994,297 | 11/1976 | Kopf .................. 128/276 |
| 4,024,866 | 5/1977 | Wallach .................. 128/276 |
| 4,223,676 | 9/1980 | Wuchinich .................. 128/276 |
| 4,246,902 | 1/1981 | Martinez .................. 128/305 |
| 4,493,694 | 1/1985 | Wuchinich .................. 604/22 |
| 4,515,583 | 5/1985 | Sorrich .................. 128/276 |
| 4,517,977 | 5/1985 | Frost .................. 128/305 |
| 4,570,632 | 2/1986 | Woods .................. 128/305 |
| 4,577,629 | 3/1986 | Martinez .................. 128/305 |
| 4,589,414 | 5/1986 | Yoshida et al. .................. 128/305 |
| 4,589,415 | 5/1986 | Haaga .................. 128/328 |
| 4,609,368 | 9/1986 | Dotson, Jr. .................. 604/35 |
| 4,662,869 | 5/1987 | Wright .................. 604/22 |
| 4,674,502 | 6/1987 | Imonti .................. 128/305 |
| 4,696,298 | 9/1987 | Higgins et al. .................. 128/305 |
| 4,706,669 | 11/1987 | Schlegel .................. 128/329 R |
| 4,753,234 | 6/1988 | Martinez .................. 128/305 |
| 4,869,715 | 9/1989 | Sherburne .................. 604/22 |
| 4,909,249 | 3/1990 | Akkas et al. .................. 606/107 |
| 4,911,161 | 3/1990 | Schechter .................. 606/171 |
| 4,922,902 | 5/1990 | Wuchinich et al. .................. 604/22 |
| 4,986,827 | 1/1991 | Akkas et al. .................. 606/107 |
| 4,989,583 | 2/1991 | Hood .................. 128/24 A |
| 5,019,035 | 5/1991 | Missirlian et al. .................. 604/22 |
| 5,106,364 | 4/1992 | Hayafuji et al. .................. 604/22 |
| 5,154,694 | 10/1992 | Kelman .................. 604/22 |
| 5,226,910 | 7/1993 | Kajiyama et al. .................. 606/171 |
| 5,250,065 | 10/1993 | Clement et al. .................. 606/172 |
| 5,261,923 | 11/1993 | Soares .................. 606/166 |
| 5,275,607 | 1/1994 | Lo et al. .................. 606/169 |
| 5,284,472 | 2/1994 | Sussman et al. .................. 604/22 |
| 5,285,795 | 2/1994 | Ryan et al. .................. 128/750 |

(List continued on next page.)

FOREIGN PATENT DOCUMENTS

| | | |
|---|---|---|
| 0232458-A2 | * 9/1996 | (EP) . |
| 0962205-A1 | * 3/1999 | (EP) . |
| WO 96/24314 | 8/1996 | (WO) . |

*Primary Examiner*—William Grant
*Assistant Examiner*—Ramesh Patel
(74) *Attorney, Agent, or Firm*—Jeffrey S. Schira

(57) ABSTRACT

A control system for a Liquefracture handpiece that uses output from a surgical console to generate a control signal for an RF amplifier. The output from the RF amplifier is used to drive the handpiece heating element. To prevent excessive heated fluid from entering the eye, the vacuum in the handpiece is monitored and excessive or rapid increases in vacuum level (indicating an occlusion or low aspiration flow) causes the power to the heating element to be reduces or eliminated.

4 Claims, 8 Drawing Sheets

U.S. PATENT DOCUMENTS

| | | | |
|---|---|---|---|
| 5,322,504 | 6/1994 | Doherty et al. | 606/167 |
| 5,359,996 | 11/1994 | Hood | 604/22 |
| 5,423,330 | 6/1995 | Lee | 128/753 |
| 5,562,692 | 10/1996 | Bair | 606/167 |
| 5,591,184 | 1/1997 | McDonnell | 606/167 |
| 5,616,120 * | 4/1997 | Andrew et al. | 604/28 |
| 5,653,692 | 8/1997 | Masterson et al. | 606/170 |
| 5,669,923 | 9/1997 | Gordon | 606/127 |
| 5,674,226 | 10/1997 | Doherty et al. | 606/107 |
| 5,865,790 | 2/1999 | Bair | 604/35 |
| 5,997,499 * | 12/1999 | Sussman et al. | 604/27 |
| 6,139,571 | 10/2000 | Fuller et al. | 607/105 |
| 6,179,805 * | 1/2001 | Sussman et al. | 604/27 |
| 6,196,989 * | 3/2001 | Padget et al. | 604/27 |
| 6,206,848 * | 3/2001 | Sussman et al. | 604/27 |

* cited by examiner

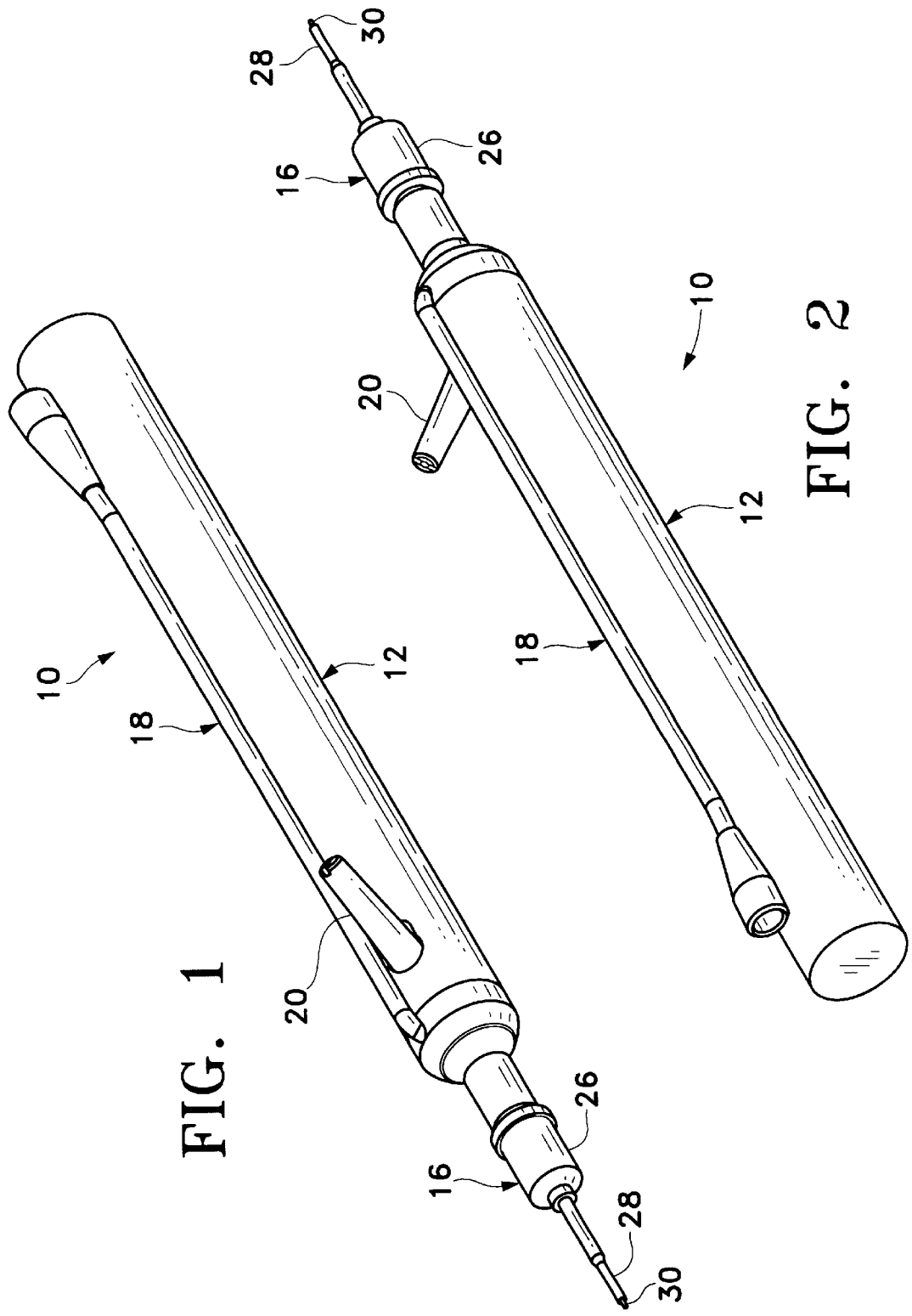

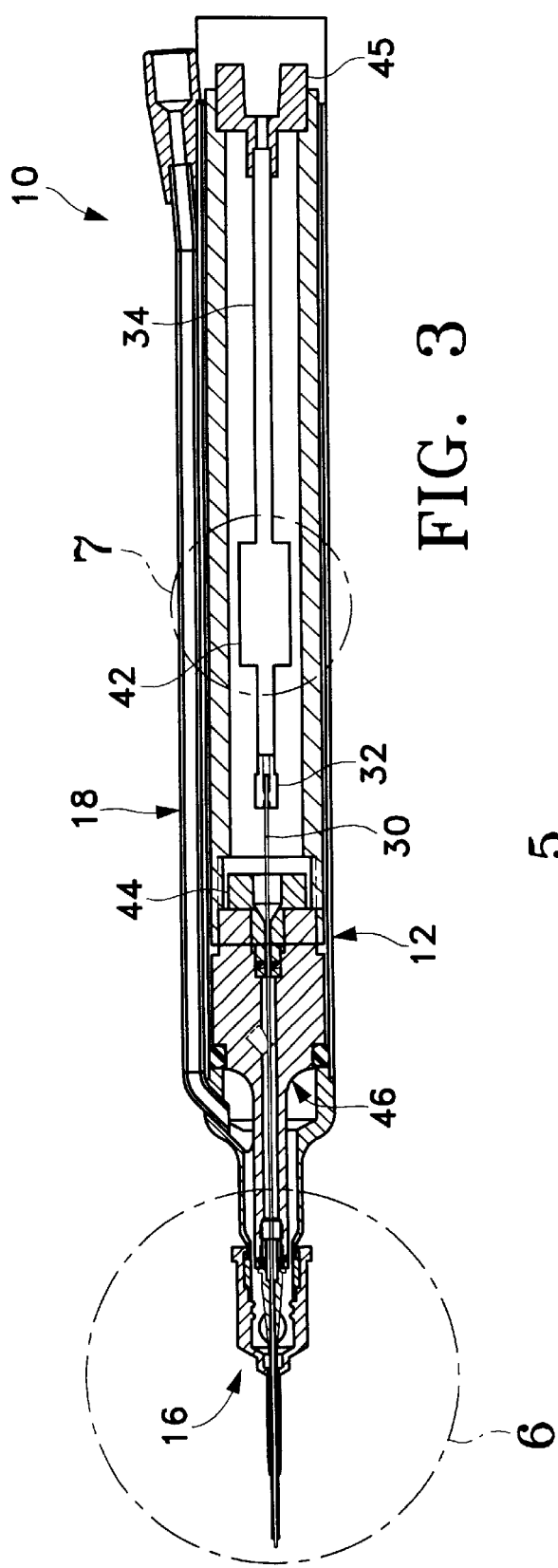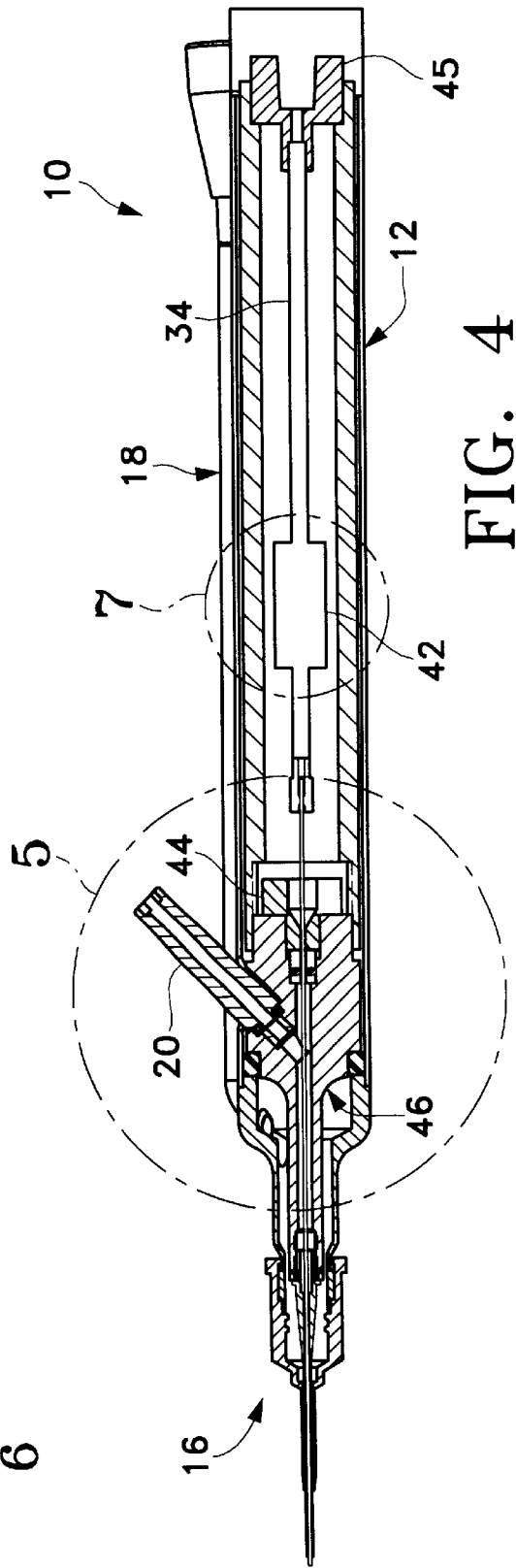

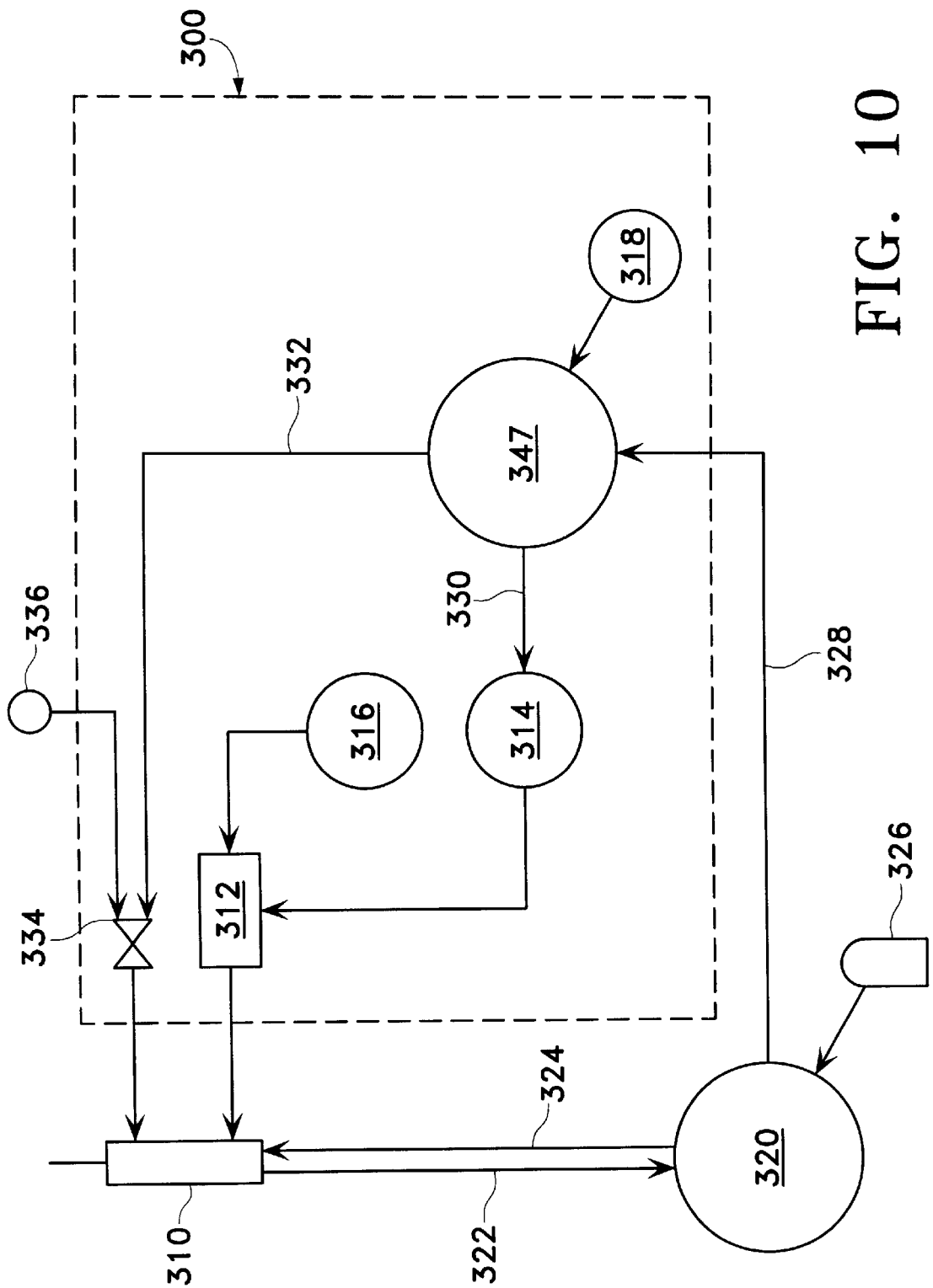

METHOD OF CONTROLLING A LIQUEFRACTURE HANDPIECE

This application is a continuation-in-part application of U.S. patent application Ser. No. 09/130,403 now abandoned, filed Aug. 6, 1998, which is a continuation-in-part application of U.S. patent application Ser. No. 09/090,433, now U.S. Pat. No. 6,080,128 filed Jun. 4, 1998.

BACKGROUND OF THE INVENTION

This invention relates generally to the field of cataract surgery and more particularly to a control system for a handpiece for practicing the Liquefracture technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens fiction by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution and the injection of a relatively cool solution, thereby quickly cooling and removing the heated solution. This technique is more fully described in U.S. Pat. No. 5,616,120 (Andrew, et al.), the entire contents of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

Therefore, a need continues to exist for a control system for a surgical handpiece that can heat internally the solution used to perform the Liquefracture technique.

BRIEF SUMMARY OF THE INVENTION

The present invention improves upon the prior art by providing a control system for a Liquefracture handpiece. The system uses output from a surgical console to generate a control signal for an RF amplifier. The output from the RF amplifier is used to drive the handpiece heating element. To prevent excessive heated fluid from entering the eye, the vacuum in the aspiration tubing is monitored and excessive or rapid increases in vacuum level (indicating an occlusion) causes the power to the heating element to be reduces or eliminated.

Accordingly, one objective of the present invention is to provide a surgical console control system.

Another objective of the present invention is to provide a surgical console control system that generates a control signal for an RF amplifier.

Another objective of the present invention is to provide a surgical console control system that provided a drive signal for a Liquefracture handpiece.

These and other advantages and objectives of the present invention will become apparent from the detailed description and claims that follow.

BRIEF DESCRIPTION OF THE DRAWINGS

FIG. 1 is a front, upper left perspective view of the handpiece of the present invention.

FIG. 2 is a rear, upper right perspective view of the handpiece of the present invention.

FIG. 3 is a cross-sectional view of the handpiece of the present invention taken along a plane passing through the irrigation channel.

FIG. 4 is a cross-sectional view of the handpiece of the present invention taken along a plane passing through the aspiration channel.

FIG. 10 is a block diagram of a control system that can be used with the handpiece of the present invention.

DETAILED DESCRIPTION OF THE INVENTION

Figure 6:
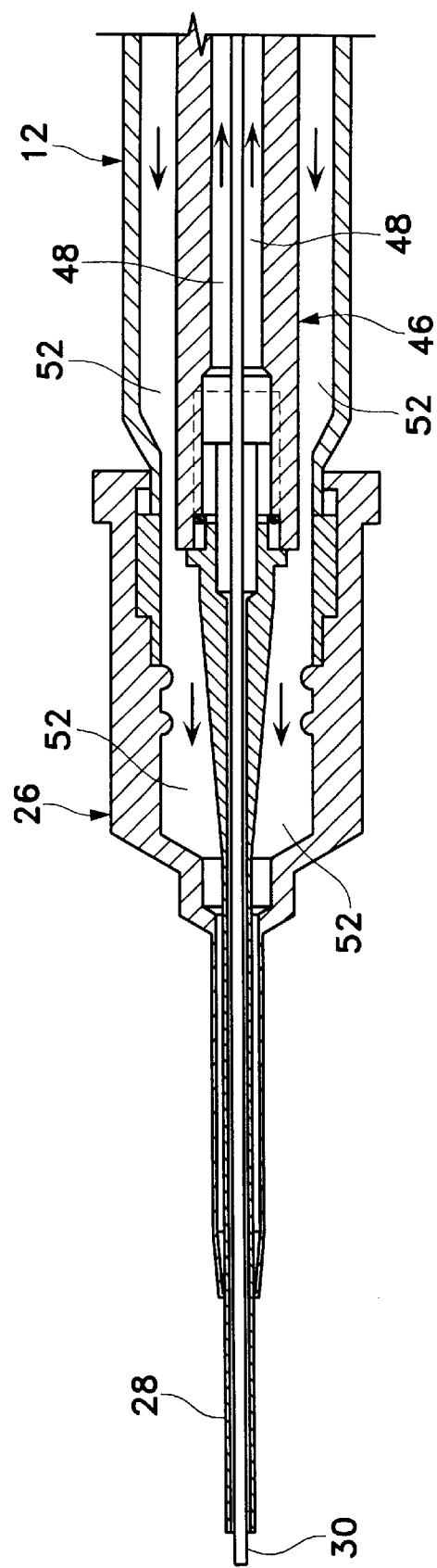
FIG. 6 is an enlarged partial cross-sectional view of the handpiece of the present invention taken at circle 6 in FIG. 3.

Handpiece 10 of the present invention generally includes handpiece body 12 and operative tip 16. Body 12 generally includes external irrigation tubing 18 and aspiration fitting 20. Body 12 is similar in construction to well-known in the art phacoemulsification handpieces and may be made from plastic, titanium or stainless steel. As best seen in FIG. 6, operative tip 16 includes tip/cap sleeve 26, needle 28 and tubing 30. Sleeve 26 may be any suitable commercially available phacoemulsification tip/cap sleeve or sleeve 26 may be incorporated into other tubes as a multi-lumen tube. Needle 28 may be any commercially available hollow phacoemulsification cutting tip, such as the TURBOSONICS tip available from Alcon Laboratories, Inc., Fort Worth, Tex. Tubing 30 may be any suitably sized tubing to fit within needle 28, for example 29 gauge hypodermic needle tubing.

Figure 5:
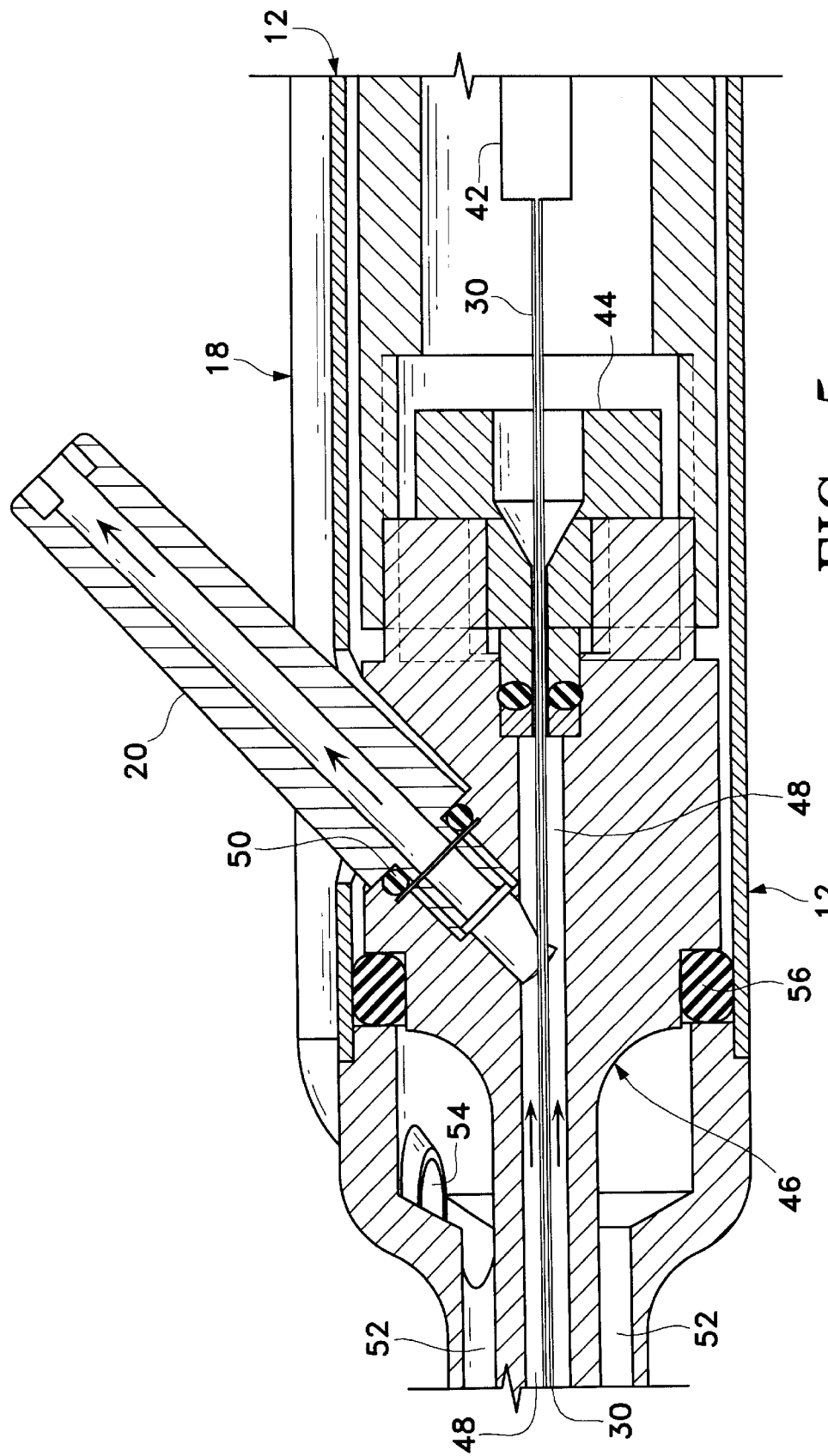
FIG. 5 is an enlarged partial cross-sectional view of the handpiece of the present invention taken at circle 5 in FIG. 4.

As best seen in FIG. 5, tubing 30 is free on the distal end and connected to pumping chamber 42 on the proximal end. Tubing 30 and pumping chamber 42 may be sealed fluid tight by any suitable means having a relatively high melting point, such as silver solder. Fitting 44 holds tubing 30 within bore 48 of aspiration horn 46. Bore 48 communicates with fitting 20, which is journaled into horn 46 and sealed with O-ring seal 50 to form an aspiration pathway through horn 46 and out fitting 20. Horn 46 is held within body 12 by O-ring seal 56 to form irrigation lumen 52 which communicates with irrigation tubing 18 at port 54.

Figure 7:
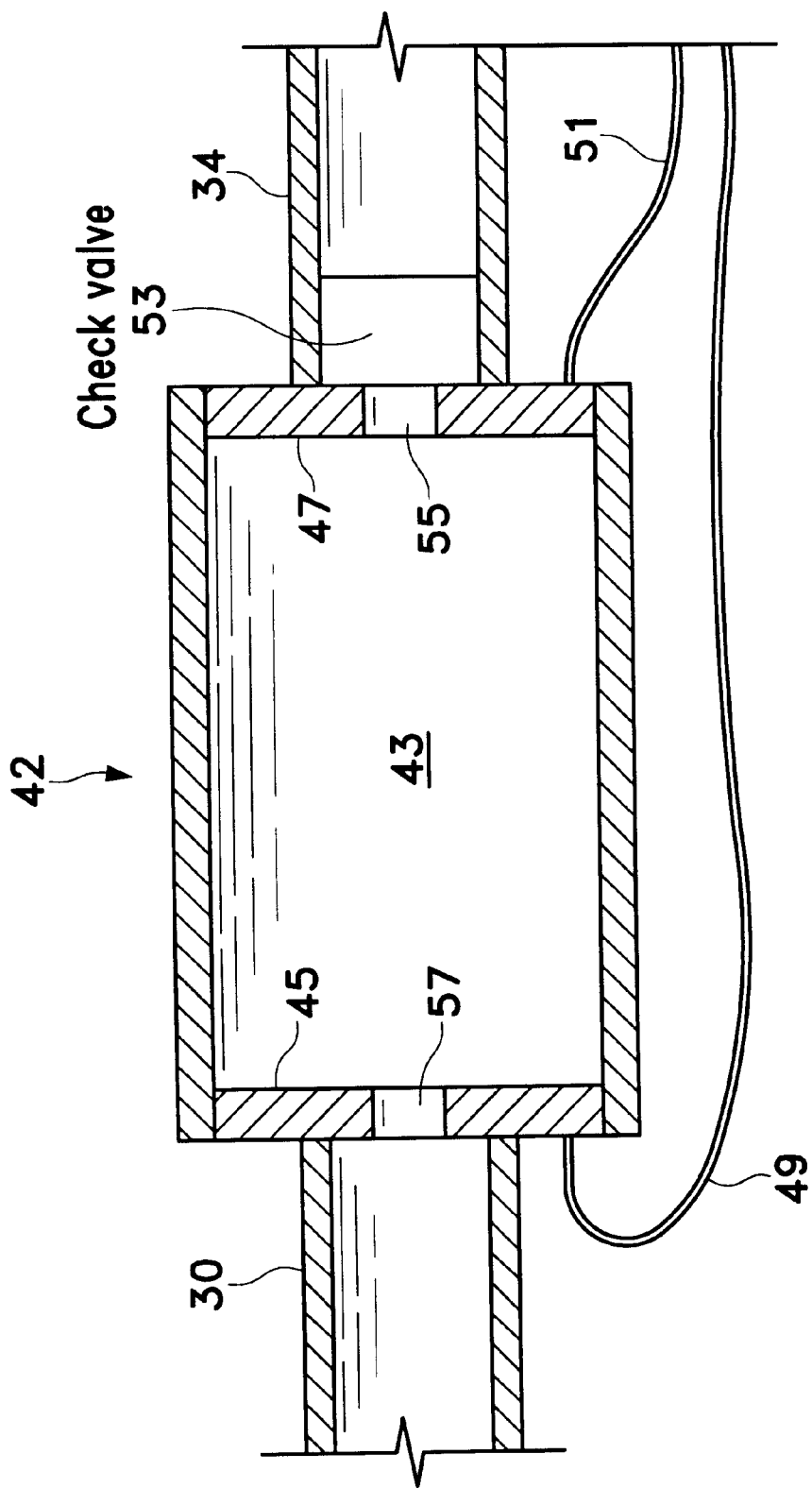
FIG. 7 is an enlarged cross-sectional view of the handpiece of the present invention taken at circle 7 in FIGS. 3 and 4, and showing a resistive boiler pump.

As best seen in FIG. 7, in a first embodiment of the present invention, pumping chamber 42 contains a relatively large pumping reservoir 43 that is sealed on both ends by electrodes 45 and 47. Electrical power is supplied to electrodes 45 and 47 by insulated wires 49 and 51, respectively. In use, surgical fluid (e.g. saline irrigating solution) enters reservoir 43 through port 55, tubing 34 and check valve 53, check valves 53 being well-known in the art. Electrical current (preferably Radio Frequency Alternating Current or RFAC) is delivered to and across electrodes 45 and 47 because of the conductive nature of the surgical fluid. As the current flows through the surgical fluid, the surgical fluid boils. As the surgical fluid boils, it expands rapidly out of pumping chamber 42 through port 57 and into tubing 30 (check valve 53 prevents the expanding fluid from entering tubing 34). The expanding gas bubble pushes the surgical fluid in tubing 30 downstream of pumping chamber 42 forward. Subsequent pulses of electrical current form sequential gas bubbles that move surgical fluid down tubing 30. The size and pressure of the fluid pulse obtained by pumping chamber 42 can be varied by varying the length, timing and/or power of the electrical pulse sent to electrodes 45 and 47 and by varying the dimensions of reservoir 43. In addition, the surgical fluid may be preheated prior to entering pumping chamber 42. Preheating the surgical fluid will decrease the power required by pumping chamber 42 and/or increase the speed at which pressure pulses can be generated.

While several embodiments of the handpiece of the present invention are disclosed, any handpiece producing adequate pressure pulse force, rise time and frequency may also be used. For example, any suitable handpiece producing a pressure pulse force of between 0.03 grams and 50.0 grams (between 1 gram and 50.0 grams being preferred), with a rise time of between 1 gram/second and 50,000 grams/second (with between 500 grams/second and 50,000 grams/second being preferred) and a frequency of between 1 Hz and 200 Hz may be used, with between 10 Hz and 100 Hz being most preferred. The pressure pulse force and frequency may be varied with the hardness of the material being removed. For example, the inventors have found that a lower frequency with a higher pulse force is more efficient at debulking and removing the relatively hard nuclear material, with a higher frequency and lower pulse force being useful in removing softer epinuclear and cortical material. Infusion pressure, aspiration flow rate and vacuum limit are similar to current phacoemulsification techniques.

Figure 8:
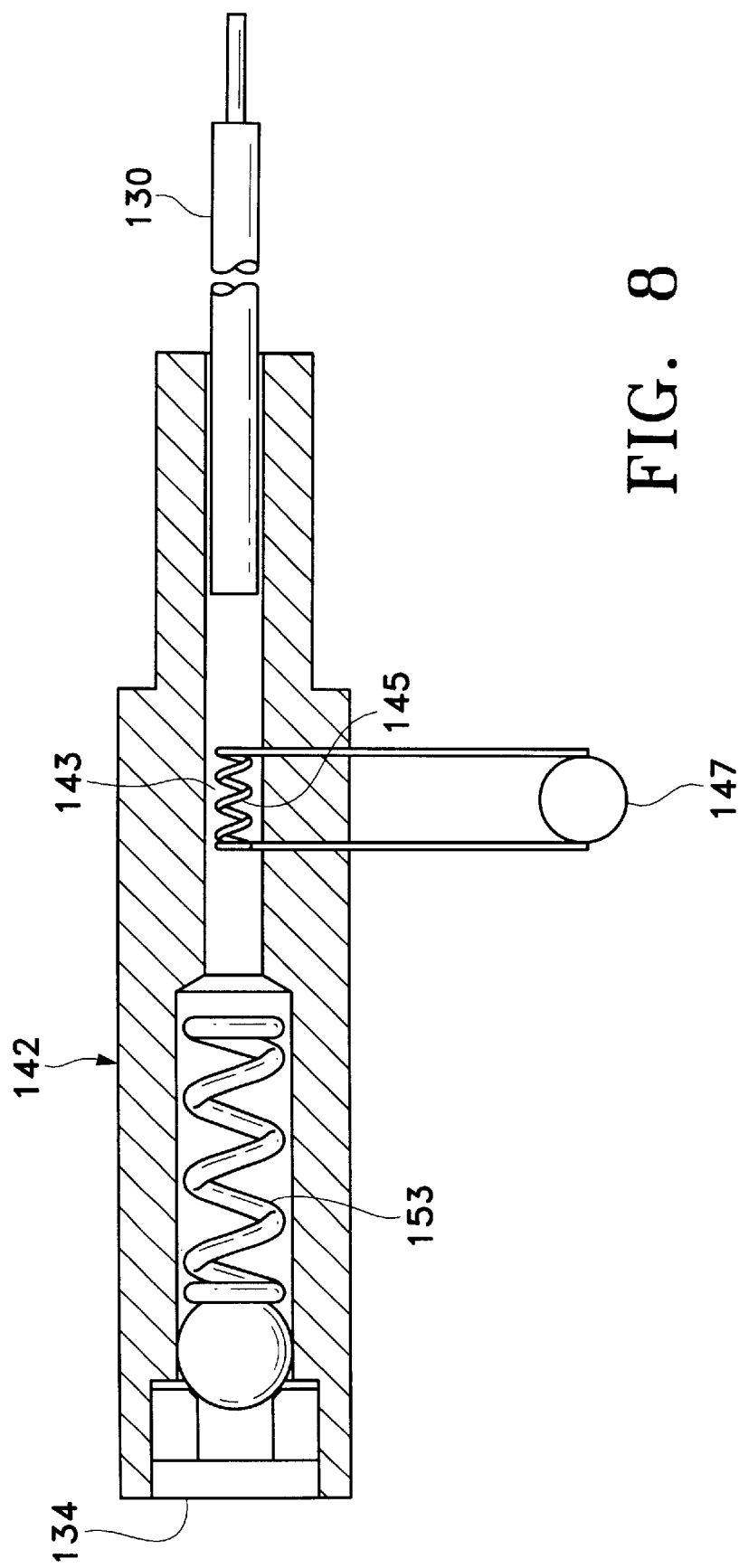
FIG. 8 is a schematic cross-sectional view of a heating element boiler pump that may be used with the present invention.

As best seen in FIG. 8, the fluid in reservoir 143 in pumping chamber 142 may also be heated by the use of heating element 145 that is internal to reservoir 143. Heating element 145 may be, for example, a coil of 0.003 inch diameter stainless steel wire which is energized by power source 147. The size and pressure of the fluid pulse obtained by pumping chamber 142 can be varied by varying the length and timing of the electrical pulse sent to element 145 by control module 147 and by varying the dimensions of reservoir 143.

As seen in FIG. 10, one embodiment of control system 300 for use in operating handpiece 310 includes control module 347, power gain RF amplifier 312 and fiction generator 314. Power is supplied to RF amplifier 312 by DC power supply 316, which preferably is an isolated DC power supply operating at several hundred volts, but typically ±200 volts. Control module 347 may be any suitable microprocessor, micro controller, computer or digital logic controller and may receive input from operator input device 318. Function generator 314 provides the electric wave form in kilohertz to amplifier 312 and typically operates at around 450 KHz or above to help minimize corrosion.

In use, control module 347 receives input from surgical console 320. Console 320 may be any commercially available surgical control console such as the LEGACY® SERIES TWENTY THOUSANDS® surgical system available from Alcon Laboratories, Inc., Fort Worth, Tex. Console 320 is connected to handpiece 310 through irrigation line 322 and aspiration line 324, and the flow through lines 322 and 324 is controlled by the user via footswitch 326. Irrigation and aspiration flow rate information in handpiece 310 is provided to control module 347 by console 320 via interface 328, which may be connected to the ultrasound handpiece control port on console 320 or to any other output port. Control module 347 uses footswitch 326 information provided by console 320 and operator input from input device 318 to generate two control signals 330 and 332. Signal 332 is used to operate pinch valve 334, which controls the surgical fluid flowing from fluid source 336 to handpiece 310. Fluid from fluid source 336 is heated in the manner described herein. Signal 330 is used to control function generator 314. Based on signal 330, function generator 314 provides a wave form at the operator selected frequency and amplitude determined by the position of footswitch 326 to RF amplifier 312 which is amplified to advance the powered wave form output to handpiece 310 to create heated, pressurized pulses of surgical fluid.

Figure 9:
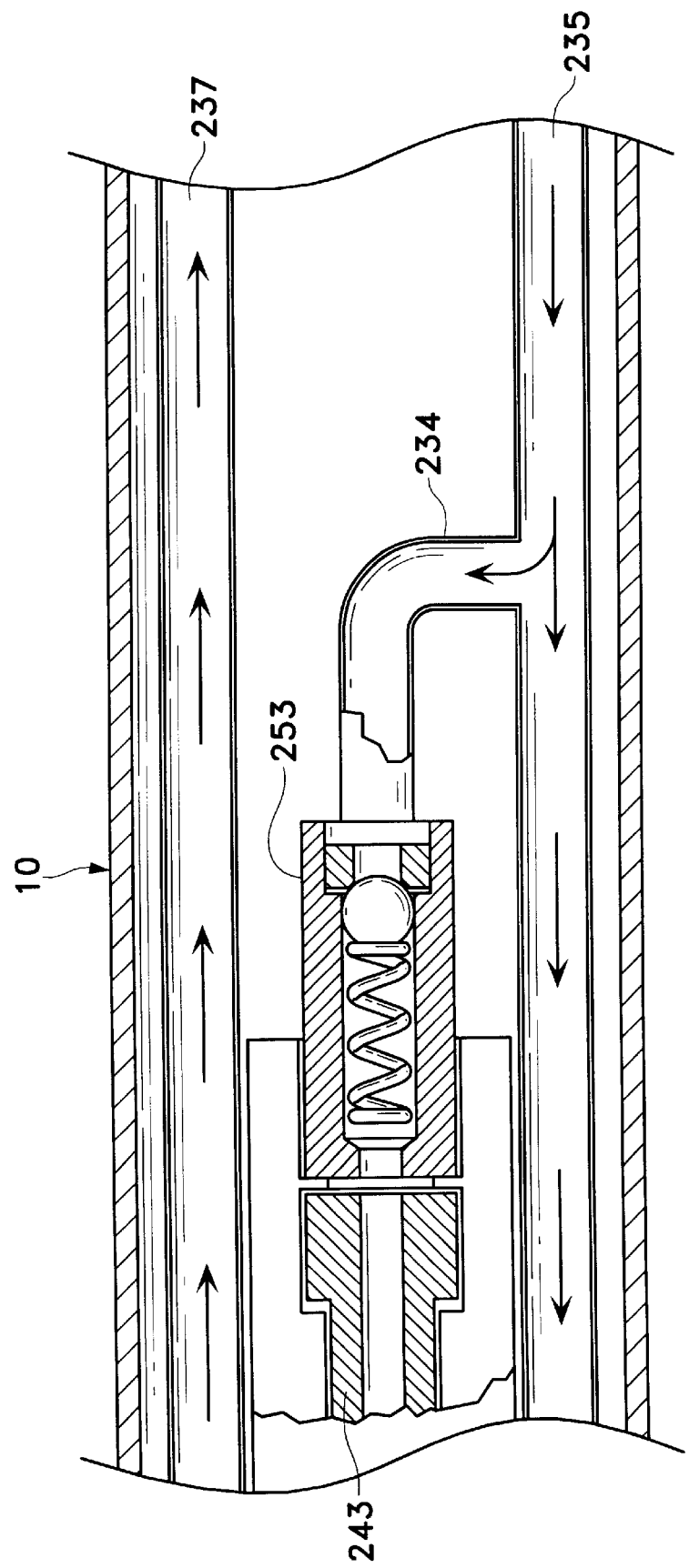
FIG. 9 is an exploded, partial cross-section view of one embodiment of the handpiece of the present invention.

As best seen in FIGS. 3, 4 and 7, surgical fluid may be supplied to pumping chamber 43 through tubing 34 or, as seen in FIG. 9, surgical fluid may be supplied to pumping chamber 243 through irrigation fluid tubing 234 which branches off main irrigation tubing 235 supplying cool surgical fluid to the operative site. As seen in FIG. 9, aspiration tubing 237 may be contained internally to handpiece 10.

Referring back to FIG. 10, any of a number of methods can be employed in order limit the amount of heat introduced into the eye. For example, the pulse train duty cycle of the heated solution can be varied so that the total amount of heated solution introduced into the eye does not vary with the pulse frequency. Alternatively, the aspiration flow rate can be varied as a function of pulse frequency so that as pulse frequency increases aspiration flow rate increases proportionally. In addition, any unexpected excessive or sharp increase in vacuum level in line 324 can indicate an occlusion or low flow in line 324. Reduced aspiration flow in line 324 may allow excessive heat build up within the surgical site. To prevent excessive heated fluid from entering the eye in the event of an occlusion in handpiece 310, aspiration flow rate information in line 324 is provided to control module 347 by console 320 via interface 328. Based on a sensed occluded or low flow condition, control module 347 can reduce or cut off the output of amplifier 312, thereby reducing or eliminating the heated fluid entering the surgical site.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

I claim:

1. A method for controlling a Liquefracture handpiece, comprising the steps of:
   a) providing a control module capable of generating a control signal;
   b) providing a function generator that receives the control signal, the function generator capable of generating a wave form in response to the control signal;
   c) providing an amplifier that receives the wave form, the amplifier capable of amplifying the wave form to provide a power wave form to the Liquefracture handpiece; and
   d) varying the output of the amplifier based on aspiration fluid flow levels.

2. The method of claim 1 wherein the control module is a microprocessor.

3. The method of claim 1 wherein the function generator operates at around 450 KHz or above.

4. The method of claim 1 wherein the amplifier is an RF amplifier.

* * * * *